US007101858B2

(12) United States Patent
Avrutov et al.

(10) Patent No.: US 7,101,858 B2
(45) Date of Patent: Sep. 5, 2006

(54) PROCESSES FOR PREPARING CLARITHROMYCIN AND CLARITHROMYCIN INTERMEDIATE, ESSENTIALLY OXIME-FREE CLARITHROMYCIN, AND PHARMACEUTICAL COMPOSITION COMPRISING THE SAME

(75) Inventors: Ilya Avrutov, Bat Hefer (IL); Igor Lifshitz, Petach Tikva (IL); Elizabeth Lewiner, Tel Aviv Jaffa (IL)

(73) Assignee: Teva Pharmaceutical Industries, Ltd., Petah Tiqva (IL)

( * ) Notice: Subject to any disclaimer, the term of this patent is extended or adjusted under 35 U.S.C. 154(b) by 0 days.

(21) Appl. No.: 10/435,141

(22) Filed: May 9, 2003

(65) Prior Publication Data
US 2003/0216556 A1    Nov. 20, 2003

Related U.S. Application Data

(63) Continuation of application No. 09/736,447, filed on Dec. 15, 2000, now Pat. No. 6,617,436.

(60) Provisional application No. 60/185,888, filed on Feb. 29, 2000, provisional application No. 60/189,120, filed on Mar. 14, 2000, provisional application No. 60/213,239, filed on Jun. 22, 2000.

(51) Int. Cl.
*A61K 31/70* (2006.01)
*C07H 17/08* (2006.01)

(52) U.S. Cl. .......................................... 514/29; 536/7.2
(58) Field of Classification Search ................ 536/7.2, 536/18.5; 514/29
See application file for complete search history.

(56) References Cited

U.S. PATENT DOCUMENTS

| | | | |
|---|---|---|---|
| 4,331,803 A | 5/1982 | Watanabe et al. | |
| 4,349,545 A | 9/1982 | D'Ambrieres et al. | |
| 4,640,910 A | 2/1987 | Faubl et al. | |
| 4,670,549 A | 6/1987 | Morimoto et al. | |
| 4,672,056 A | 6/1987 | Fernandes et al. | |
| 4,672,109 A | 6/1987 | Watanabe et al. | |
| 4,680,386 A | 7/1987 | Morimoto et al. | |
| 4,957,905 A | 9/1990 | Hunt | |
| 4,990,602 A | 2/1991 | Morimoto et al. | |
| 5,274,085 A | 12/1993 | Amano et al. | |
| 5,719,272 A | 2/1998 | Yang et al. | |
| 5,756,473 A | 5/1998 | Liu et al. | |
| 5,808,017 A | 9/1998 | Chang | |
| 5,837,829 A * | 11/1998 | Ku | 536/7.4 |
| 5,844,105 A * | 12/1998 | Liu et al. | 536/18.5 |
| 5,852,180 A | 12/1998 | Patel | |
| 5,858,986 A | 1/1999 | Liu et al. | |
| 5,864,023 A | 1/1999 | Ku et al. | |
| 5,872,229 A | 2/1999 | Liu et al. | |
| 5,892,008 A | 4/1999 | Ku et al. | |
| 5,932,710 A | 8/1999 | Liu et al. | |
| 5,945,405 A | 8/1999 | Spanton et al. | |
| 6,506,886 B1 | 1/2003 | Lee et al. | |
| 6,617,436 B1 * | 9/2003 | Avrutov et al. | 536/7.2 |
| 6,624,292 B1 | 9/2003 | Lifshitz et al. | |

FOREIGN PATENT DOCUMENTS

| | | |
|---|---|---|
| CA | 1 225 637 | 8/1987 |
| EP | 0 158 467 A2 | 10/1985 |
| EP | 0 158 467 B1 | 10/1985 |
| EP | 0 180 415 A2 | 5/1986 |
| EP | 0 180 415 B1 | 5/1986 |
| EP | 0 272 110 A3 | 6/1988 |
| EP | 0 272 110 B1 | 6/1988 |
| WO | 98/04573 | 2/1998 |
| WO | 98/04574 | 2/1998 |
| WO | 98/31699 | 7/1998 |
| WO | 00/14099 | 3/2000 |

OTHER PUBLICATIONS

Y. Watanabe, et al., Chemical Modification of Erythromycins: IX. Selective Methylation At the C-6 Hydroxyl Group of Erythromycin A Oxime Derivatives and Preparation of Clarithromycin, vol. 46 No. 4 The Journal of Antibiotics, pp. 647-660 (1993).

* cited by examiner

*Primary Examiner*—Elli Peselev
(74) *Attorney, Agent, or Firm*—Kenyon & Kenyon LLP

(57) ABSTRACT

The present invention relates to processes for preparing protected silylated clarithromycin oxime, preferably 6-O-methyl-2',4"-bis(trimethylsilyl)-erythromycin A 9-O-(2-methoxyprop-2-yl)oxime ("S-MOP oxime"), and for converting protected silylated clarithromycin oxime, preferably S-MOP oxime, to clarithromycin. Processes for preparing protected silylated clarithromycin oxime according to the present invention, include reacting a silyl oxime derivative with methylating agent in the presence of at least one solvent and a base, where the solvent comprises methyl tertbutyl ether. Processes for converting protected silylated clarithromycin oxime to clarithromycin according to the present invention, include reacting protected silylated clarithromycin oxime with ethanol and water at an ethanol to water ratio of about 1:1, in the presence of an acid and a deoximating agent and cooling the reaction mixture prior to adding sodium hydroxide, where the process takes place without any additional water addition. Further processes for converting protected silylated clarithromycin oxime to clarithromycin, include heating a mixture of protected silylated clarithromycin oxime, acid, and deoximating agent in an ethanol/water solvent to reflux for more than 4 hours, with a two-fold addition of deoximating agent to produce essentially oxime-free clarithromycin.

9 Claims, No Drawings

PROCESSES FOR PREPARING CLARITHROMYCIN AND CLARITHROMYCIN INTERMEDIATE, ESSENTIALLY OXIME-FREE CLARITHROMYCIN, AND PHARMACEUTICAL COMPOSITION COMPRISING THE SAME

CROSS REFERENCE TO RELATED APPLICATION

This application is a continuation of U.S. patent application Ser. No. 09/736,447, filed Dec. 15, 2000, now U.S. Pat. No. 6,617,436, which claims the benefits of U.S. Provisional Application Nos. 60/185,888, filed Feb. 29, 2000; 60/189,120, filed Mar. 14, 2000 and 60/213,239, filed Jun. 22, 2000, the disclosures of all of which are incorporated herein by reference.

FIELD OF THE INVENTION

The present invention relates to methods for preparing a protected silylated clarithromycin oxime, such as 6-O-methyl-2',4''-bis(trimethylsilyl)-erythromycin A 9-O-(2-methoxyprop-2-yl)oxime (hereinafter "S-MOP oxime"), which include reacting a silyl oxime derivative with methylating agent while stirring in the presence of at least one solvent, where the solvent includes at least methyl tert-butyl ether (MTBE), and a base.

The present invention also relates to a method of converting the protected silylated clarithromycin oxime to clarithromycin, which includes reacting the protected silylated clarithromycin oxime with acid and deoximating agent in the presence of ethanol and water at an ethanol to water ratio of about 1:1. The reaction mixture is cooled to about 20° C. and a base, preferably sodium hydroxide, is added. The method does not include any additional water addition to process clarithromycin.

The present invention further relates to a method of converting a protected silylated clarithromycin oxime, such as S-MOP oxime, to clarithromycin, which includes heating a mixture of the protected silylated clarithromycin oxime, acid, and deoximating agent in an ethanol/water solvent to reflux for more than 4 hours, with a two-fold addition of said deoximating agent. The invention further relates to the essentially oxime-free clarithromycin produced by such a method and pharmaceutical compositions containing the same.

BACKGROUND OF THE INVENTION

6-O-methyl erythromycin A (clarithromycin) is a semi synthetic macrolide antibiotic related to erythromycin A. It exhibits excellent antibacterial activity against gram-positive bacteria, some gram-negative bacteria, anaerobic bacteria, Mycoplasma, and Chlamydia. It is stable under acidic conditions and is efficacious when administered orally. Clarithromycin is a useful therapy for infections of the upper respiratory tract in children and adults. Clarithromycin is stable under acidic conditions and is efficacious when administered orally.

The chemical structure of clarithromycin is:

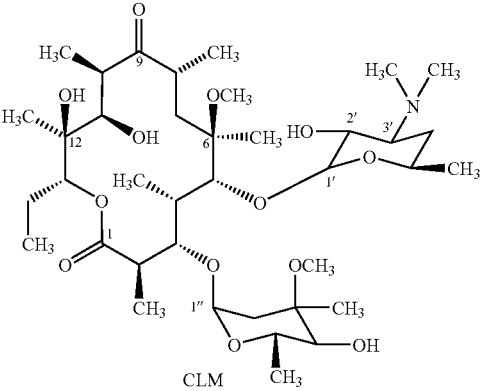

Various methods of preparing 6-O-methylerythromycin A from erythromycin A have been described in the patent literature. One of the most effective methods includes the following steps: 1) protecting the 9-oxo group with a substituted oxime group, 2) protecting the hydroxyl groups in positions 2' and 4'', 3) methylating the hydroxyl in position 6 to give a protected sililated clarithromycin oxime, and 4) removing the protecting groups at the 2', 4'' and 9 position.

The third step, which comprises methylating the hydroxyl group at position 6, is performed in the presence of a solvent. This 6-O-methylation of various erythromycin derivatives in converting erythromycin A to clarithromycin has been reported in several U.S. Patents including U.S. Pat. Nos. 4,680,386 and 4,672,109.

U.S. Pat. No. 4,680,386 for example, describes a method of methylating the hydroxyl group at the 6 position by reacting the compound with a methylating agent in the presence of a base in an aprotic solvent at a temperature of between 0° C. and room temperature. The '386 patent describes the use of solvents including N,N-dimethylformamide, dimethyl sulfoxide, hexamethylphosphoric triamide, and a mixture of one or more of these solvents. U.S. Pat. No. 4,672,109 describes the use of solvents such as dimethyl sulfoxide, N,N-dimethylformamide, hexamethyl phosphoric triamide, a mixture of two or more of these solvents or a mixture of one of these solvents and tetrahydrofuran, 1,2-dimethoxyethane and the like. The '109 patent further describes a preferred embodiment of this step using a mixture of dimethyl sulfoxide and tetrahydrofuran. WO 97/19096 describes a mixture of solvents including N,N-dimethylformamide, dimethyl sulfoxide, N-methyl-2-pyrrolidone, hexamethyl phosphoric triamide, tetrahydrofuran, 1,2-dimethoxyethane, acetonitrile and ethyl acetate for use in the methylating step.

However, several of the above-described solvents are expensive, do not enable selective methylation, produce significant unwanted side products and/or cause complications during later phase separation steps.

The fourth step includes removing the protecting groups, and thus, converts protected silylated clarithromycin oxime to clarithromycin. Described methods of converting a protected silylated clarithromycin oxime, such as S-MOP oxime, to clarithromycin include reacting the protected silylated clarithromycin oxime with ethanol in the presence of an acid and a deoximating agent. The product of the reaction is then washed with water one or more times. The ethanol generally also contains water.

U.S. Pat. No. 4,990,602 has an ethanol to water ratio of 1:4 and does not involve cooling. U.S. Pat. No. 4,670,549 adds sodium hydroxide after cooling at an ethanol to water ratio of 1:3. Neither of these methods lowers the impurity content of clarithromycin.

SUMMARY OF THE INVENTION

The present invention relates to methods for preparing a protected silylated clarithromycin oxime, such as 6-O-methyl-2',4"-bis(trimethylsilyl)-erythromycin A 9-O-(2-methoxyprop-2-yl)oxime ("S-MOP oxime"), which include reacting a silyl oxime derivative with methylating agent while stirring in the presence of at least one solvent and a base, where the solvent includes methyl tert-butyl ether (MTBE). In the method for preparing the protected silylated clarithromycin oxime, the methylating agent is preferably one or more of methyl iodide, methyl bromide, dimethylsulfate, methyl p-toluenesulfonate, or methanesulfonate. The base is preferably sodium hydride, potassium hydroxide, or sodium hydroxide.

Further embodiments of the present invention relates to methods of converting a protected silylated clarithromycin oxime, such as S-MOP oxime, to clarithromycin. One such method includes reacting the protected silylated clarithromycin oxime with acid and a deoximating agent in the presence of ethanol and water at an ethanol to water ratio of about 1:1. The reaction mixture is cooled to about 20° C. and a base, preferably sodium hydroxide solution, is added. In this method, no additional water is added to process clarithromycin. Another method of converting a protected silylated clarithromycin oxime to clarithromycin includes heating a mixture of the protected silylated clarithromycin oxime, acid, and deoximating agent in an ethanol/water solvent to reflux for more than 4 hours, with a two-fold addition of deoximating agent. In the latter method, essentially oxime-free clarithromycin is produced, which contains less than 40 ppm of the corresponding oxime intermediate.

DETAILED DESCRIPTION OF THE INVENTION

Clarithromycin is described, inter alia, in the following publications, which are hereby incorporated herein by reference: U.S. Pat. Nos. 3,922,379, 4,331,803, 4,670,549, 4,672,109, 4,680,386, 4,808,411, 4,957,905, 4,990,602, 5,837,829, 5,844,105, 5,852,180, 5,858,986, 5,919,489, 5,932,710, and 5,945,405.

The terms "6-O-methylerythromycin A" and "clarithromycin" are used interchangeably herein and are meant to include clarithromycin in any form (such as crystalline Form 0, Form I, Form II or Form IV) or pharmaceutical salts thereof or mixtures thereof, as well as amorphous solids, syrups, or semisolids comprising clarithromycin in any state of purity, unless specified otherwise.

The present invention relates to increasing the product yield and unwanted side effects produced various steps included in converting erythromycin A to clarithromycin. Clarithromycin is prepared from erythromycin A by a variety of synthetic routes. Some of these routes include oximation steps and the use of a protected silylated clarithromycin oxime, such as an S-MOP oxime intermediate.

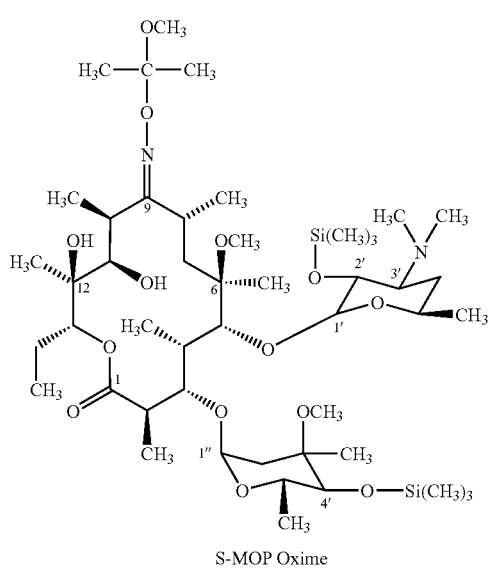

S-MOP Oxime

The synthetic routes of converting erythromycin A to clarithromycin that are improved herein, are those that utilize a protected silylated clarithromycin oxime intermediate, such an S-MOP oxime intermediate.

Synthetic routes of converting erythromycin A to clarithromycin include methylation of the 6-hydroxy group of erythromycin A. In the conversion process it is necessary to protect various groups, such as the hydroxy groups at the 2' and 4" positions of erythromycin A, which are potentially reactive with alkylating agents, prior to alkylation of the 6-hydroxy group. Examples of methods of preparing clarithromycin using oxime intermediates are described for example, in U.S. Pat. Nos. 4,990,602 and 5,858,986, which each describe a method of preparing clarithromycin from erythromycin A by oximation of the C-9 carbonyl, protection of the C-2' and C-4" hydroxy groups, methylation of the C-6 hydroxy group, and deoximation and removal of the protecting groups.

An example of a synthetic route of converting erythromycin A to clarithromycin via oximation, that utilizes a protected silylated clarithromycin oxime, specifically S-MOP oxime, as an intermediate, is as follows in Scheme 1 (each compound in the process is numbered for ease of referencing them herein).

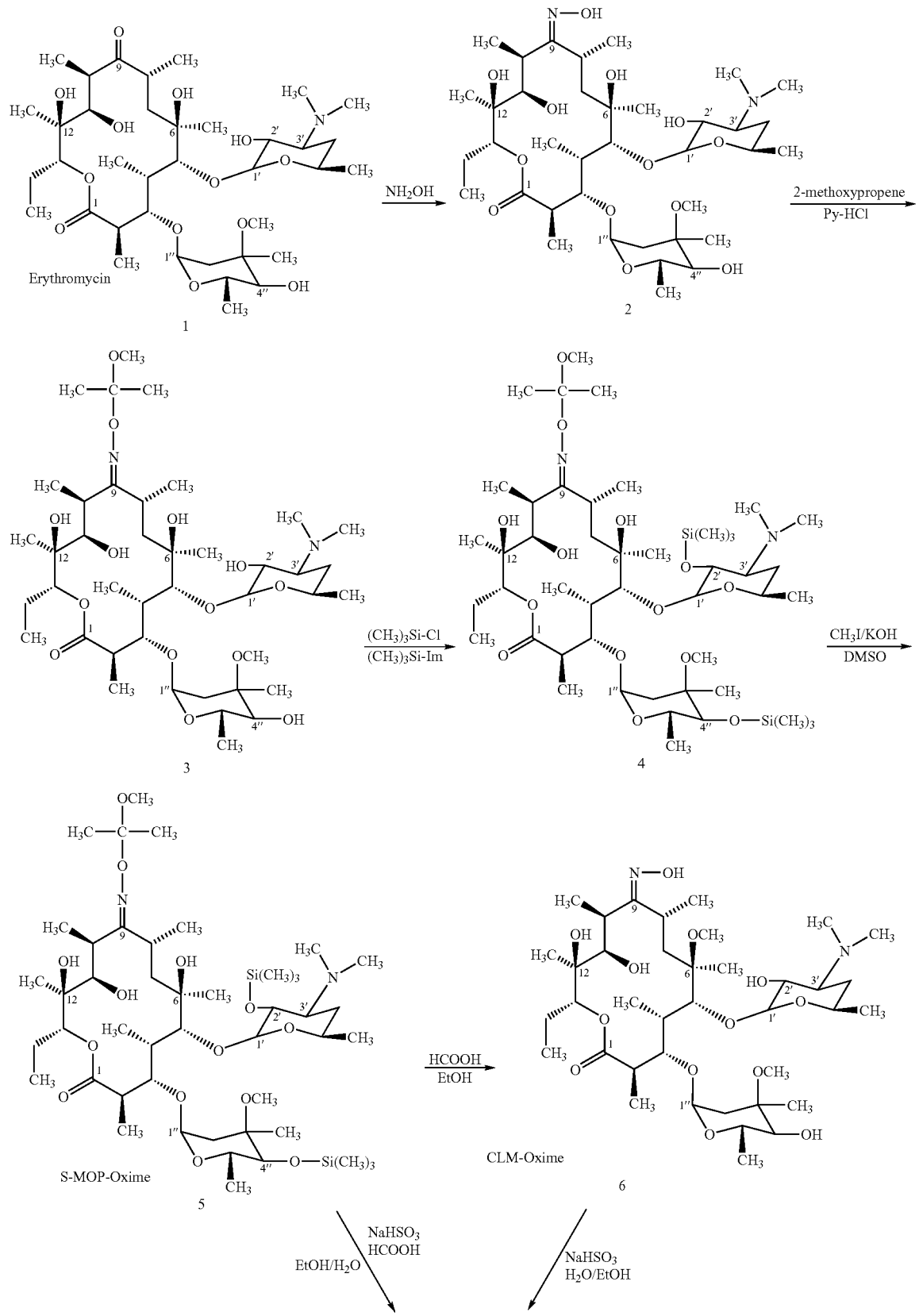

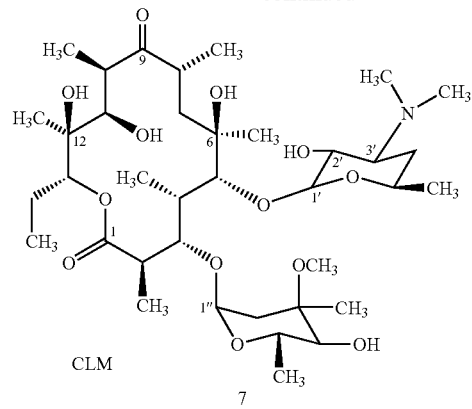

CLM

The present invention is directed to improved methods of preparing a protected silylated clarithromycin oxime, preferably an S-MOP oxime (compound 5 in Scheme 1) from a 9-oxim silyl derivative (such as compound 4 in Scheme 1) and of converting a protected silylated clarithromycin oxime, preferably an S-MOP oxime (compound 7 in Scheme 1), to clarithromycin.

The methods described herein are not limited to use in the process shown in Scheme 1. Scheme 1 is provided as a representative scheme in which a protected silylated clarithromycin oxime, such as an S-MOP oxime, is prepared from a silyl derivative and another step includes converting the protected silylated clarithromycin oxime to clarithromycin. It would be understood by those in the art that the methods described herein may be used in various schemes for converting erythromycin A to clarithromycin, which employ a protected silylated clarithromycin oxime compound as an intermediate therein.

In the representative process of converting erythromycin A to clarithromycin shown above in Scheme 1, erythromycin A is first converted to a protected silylated oxime, such as 2',4"-bis(trimethylsilyl)-erythromycin A 9-O-(2-methoxyprop-2-yl)oxime (compound 4 in Scheme 1), by methods generally known in the art. As indicated above, protecting groups protect certain positions from potentially reacting with alkylating agents during the subsequent methylation of the 6-hydroxy group, and also protect 3'-dimethylamino groups from quaternary alkylation.

Although the conversion from erythromycin A to a protected silylated oxime (e.g., 2',4"-bis(trimethylsilyl)-erythromycin A 9-O-(2-methoxyprop-2-yl)oxime) may be accomplished by any methods known to those in the art, in a preferred method, erythromycin A is first oximated and subsequently protecting groups are added initially to the oxime group and then to the 2' and 4" positions. Suitable methods for oximation and the addition of protecting groups are set forth in U.S. Pat. Nos. 5,858,986 and 4,990,602, which teach general methods of oximation that may be used in accordance with the present invention, such as by reacting erythromycin A with the substituted hydroxylamine $R^1ONH_2$, or by reacting erythromycin A with hydroxylamine hydrochloride in the presence of base, or hydroxylamine in the presence of acid, followed by reaction with $R^1X$, where $R^1$ is alkoxyalkyl. U.S. Pat. Nos. 5,858,986 and 4,990,602 further describe suitable methods for protecting the oxime group and two hydroxy groups (i.e., at the 2' and 4" positions) with silyl groups. The hydroxy groups may be protected simultaneously or in different steps from one another. Preferred methods of converting the silyl derivative to a protected silylated clarithromycin oxime and converting the protected silylated clarithromycin oxime to clarithromycin are set forth below.

The step of converting a silyl derivative such as compound 4 to a protected silylated clarithromycin oxime (such as S-MOP oxime) is a methylation step. In this methylation step, one or more hydroxy groups, such as that at the 6-position, is methylated. One embodiment of the present invention relates to methods for preparing a protected silylated clarithromycin oxime, which includes reacting a silyl oxime derivative with a methylating agent while stirring in the presence of a solvent and a base.

The solvent in this embodiment includes MTBE (methyl tertbutyl ether), preferably along with another aprotic solvent(s). The most preferable solvent is a mixture of DMSO (dimethyl sulfoxide) and MTBE. The present inventors have found the MTBE is more selective, cheaper and easier to recover than solvents described in the literature, including the primarily used combination of DMSO with THF (tetrahydrofuran).

In this embodiment, the silyl derivative is stirred in a solvent at about ambient temperature until the silyl derivative is dissolved. For purposes of this specification, ambient temperature is from about 20° C. to about 25° C. A further solvent may then be added. The solution is cooled to a temperature of between about 0° C. and about 20° C., preferably between about 5 and about 15° C., even more preferably about 10° C.

In this embodiment, a methylating agent is added while stirring the solution. The methylating agent is preferably an agent such as methyl iodide, methyl bromide, dimethylsulfate, methyl p-toluenesulfonate, methyl methanesulfonate, dimethyl sulfate, and the like. The methylating agent is most preferably methyl iodide. Although 1.0 to 10 molar equivalents of methylating agent can be used per mole of silyl derivative, it is sufficient to use between about 1.0 and about 3.0 molar equivalents of methylating agent per mole of silyl oxime derivative.

A base is added to the solution of silyl oxime derivative, solvent(s) and methylating agent in this embodiment, and stirred at a temperature of between about 9° C. and about 25° C., preferably between about 9° C. and about 15° C. until the reaction is essentially completed. The base is preferably one or more of sodium hydride, potassium hydroxide, sodium hydroxide, sodium hydride, potassium tert-butoxide, potassium hydride, and the like. Most preferably, the base is powdered potassium hydroxide, which is added to the solution and stirred at about 10° C. The amount of base used is usually from about 1 to about 3 molar equivalents of the silyl oxime derivative.

Preferably the temperature is maintained at about 10° C. to about 12° C. while stirring is taking place and the reaction is occurring. The progress of the reaction is monitored by HPLC.

When MTBE is used as a solvent in this embodiment, two phases may form, making it easier to separate the protected silylated clarithromycin oxime, than if other solvents are used that form a single phase. The separation of protected silylated clarithromycin oxime may be performed by conventional methods. For example, once the reaction is complete, the workup of the reaction mixture may include phase separation, washing of the MTBE layer with water and evaporation to dryness.

Another embodiment of the present invention relates to converting a protected silylated clarithromycin oxime, preferably S-MOP oxime, (whether it is arrived at by the method of the above embodiment or by another method) to clarithromycin, by reacting the protected silylated clarithromycin oxime with an acid and a deoximating agent in the presence of aqueous ethanol where the ethanol to water ratio is about 1:1. The reaction of the protected silylated clarithromycin oxime with deoximating agent and acid brings about deoximation together with elimination of the protecting groups. The reaction mixture is then cooled to between about 15° C. and about 25° C., more preferably about 20° C., and subsequently a base, preferably sodium hydroxide solution, is added.

Previously described methods of converting a protected silylated clarithromycin oxime to clarithromycin include introducing the protected silylated clarithromycin oxime into a water/ethanol system in the presence of an acid and a deoximating agent and refluxing at 80° C. Subsequently, a large amount of water is added. According to this process, the mass ratio between the protected silylated clarithromycin oxime:ethanol:water is about 1:5:5 before the addition of the large amount of water. The ratio of ethanol to water is about 1:1, before adding additional water and about 1:4 after adding additional water. Then, NaOH is added and the solution is cooled to 0° C. This method results in the precipitation of clarithromycin. However, this process is disadvantageous because it doesn't allow purification of the product from an impurity, the 11-methyl derivative of clarithromycin. This impurity is referred to as the "dimethyl" form of clarithromycin, which is difficult to remove. When the ethanol to water ratio is 1:3 or 1:4 for example, it is difficult to remove the impurity. If the reaction mixture is not cooled prior to addition of sodium hydroxide, the impurity content may not decrease.

The present invention relates to an improved process for obtaining clarithromycin from a protected silylated clarithromycin oxime, such as S-MOP oxime, in which the obtained clarithromycin contains significantly reduced amounts of the "dimethyl" impurity. The method includes reacting a protected silylated clarithromycin oxime with an acid (such as formic acid) and a deoximating agent in the presence of queous ethanol at an ethanol/water ratio of about 1:1, refluxing the solution at 80° C., cooling the solution to about 20° C., and adding NaOH.

In the present method, acid is added to the mixture of protected silylated clarithromycin oxime, ethanol, water and deoximating agent and the mixture is heated at reflux (about 80° C.) Heating is then continued and the suspension is stirred for an amount of time sufficient to finish the reaction. The mixture is then cooled to about 20° C. and sodium hydroxide solution having a concentration of from about 20% to about 47%, preferably 47%, is added at this temperature until the pH of the reaction mixture reaches about 10 to about 11, preferably about 10.2 to about 10.5. Crystalline clarithromycin is then isolated, preferably by filtration, with no further water addition. The obtained clarithromycin may subsequently be further purified and/or isolated and the crystalline form of clarithromycin may be altered to the desired form (such as crystal form 0, I, II, or IV) for use.

There is need to add no additional water in the method of the present invention. Since additional water (that is, water other than the water present with the ethanol in a ratio of about 1:1 and in sodium hydroxide solution) is not required in the present method, clarithromycin may be formed with a significant decrease in the amount of impurities.

The advantages of the present method are inter alia that the clarithromycin produced contains about 50% less of the dimethyl impurity than clarithromycin produced by other processes, and the working volumes are lower. Preferably, the volume ratio of protected silylated clarithromycin oxime:water:ethanol is about 1:3:3.

Another embodiment of the present invention also relates to converting a protected silylated clarithromycin oxime, such as S-MOP oxime, (whether it is arrived at by the method described hereinabove or by another method) to clarithromycin, by heating a mixture of a protected silylated clarithromycin oxime, acid, and two-fold addition of deoximating agent in an ethanol/water solvent to reflux for more than 4 hours. Essentially oxime-free clarithromycin, that is clarithromycin, which contains less than 40 ppm of the corresponding oxime intermediate, may be produced by this method.

As in the previous embodiment, the reaction of protected silylated clarithromycin oxime with deoximating agent and acid brings about deoximation together with elimination of the protecting groups. The reaction mixture is then cooled to between about 15° C. and about 25° C., more preferably about 20° C., and subsequently a base, preferably sodium hydroxide solution, is added.

Previously described methods of converting a protected silylated clarithromycin oxime to clarithromycin include introducing the protected silylated clarithromycin oxime into a water/ethanol system in the presence of an acid and a deoximating agent and refluxing for 2 hours in an ethanol/water solvent. The product of this process contains clarithromycin oxime as an impurity.

By two-fold addition of deoximating agent refluxing for over four hours, the clarithromycin oxime impurity is largely removed, resulting in relatively pure (essentially oxime-free) clarithromycin. Accordingly, the present invention is also directed to this essentially oxime-free clarithromycin and pharmaceutical compositions containing the essentially oxime-free clarithromycin. Pharmaceutical compositions containing clarithromycin are described for example in U.S. Pat. No. 5,858,986.

In the present method, acid is added to the mixture of S-MOP oxime, ethanol, water and deoximating agent and the mixture is heated at reflux (about 80° C.). Heating is then continued and the suspension is stirred for at least four hours. The mixture is then cooled, preferably to about 20° C. and sodium hydroxide solution having a concentration of from about 20% to about 47%, preferably 47%, is added at this temperature until the pH of the reaction mixture reaches about 10 to about 11, preferably about 10.2 to about 10.5. Crystalline clarithromycin is then isolated, preferably by filtration, with no further water addition. The obtained clarithromycin may subsequently be further purified and/or isolated and the crystalline form of clarithromycin may be altered to the desired form (such as crystal form 0, I, II, or IV) for use.

Examples of suitable deoximating agents for use in the methods of producing clarithromycin according to the present invention include inorganic sulfur oxide compounds such as sodium hydrogen sulfite, sodium pyrosulfate, sodium thiosulfate, sodium sulfite, sodium hydrosulfite, sodium metabisulfite, sodium dithionate, postassium hydrogen sulfite, potassium thiosulfate, potassium metabisulfite and the like. A particularly preferred deoximating agent is sodium metabisulfite. The amount of deoximating agent is about 1 to 10 molar equivalents, preferably 4 to 7 molar equivalents relative to the protected silylated clarithromycin oxime.

A non-limiting example of a suitable acid for use in the present invention is formic acid. The amount of formic acid added to the mixture of protected silylated clarithromycin oxime is about 1.5 to 10 molar equivalents, preferably 2 to 5 equivalents relative to the protected silylated clarithromycin oxime.

The following examples are provided to enable one skilled in the art to practice the invention and are merely illustrative of the invention. The examples should not be read as limiting the scope of the invention as defined in the claims.

EXAMPLE 1

This example is directed to a method for preparing a protected silylated clarithromycin oxime, particularly the preferred S-MOP oxime, according to the present invention. The example involves reacting a silylated erythromycin A oxime derivative with a methylating agent while stirring in the presence of at least one solvent and a base.

MTBE is charged at about ambient temperature (12 liters) and a 9-oxime silyl derivative (1 kg) is charged at about ambient temperature, stirring the 9-oxime silyl derivative in the MTBE solvent for several minutes until the silyl derivative is dissolved and a clear solution is obtained. DMSO (10.0 liters) is added to the clear solution and the solution is cooled to about 10° C. Methyl iodide (0.218 kg) is added to the solution while stirring. Powdered potassium hydroxide (0.1 kg) is also added at 10° C. with stirring.

Stirring is continued while maintaining the temperature at about 10° C. to about 12° C. The progress of the reaction is monitored by HPLC. The reaction is completed after about 60 min. After the reaction is completed it is quenched by adding dimethyl amine solution (40%, 0.6 liters) at 10–12° C. and stirring for 30 min. The stirring is then stopped and the layers are separated. The lower layer is extracted out with MTBE (4.0 liters). Both MTBE layers, from reaction and from extraction, are combined and washed with water (5.0 liters). The MTBE layer is distilled under reduced pressure to dryness to receive S-MOP oxime (crude), yield: 1.05 kg. The DMSO layer is taken for recovery.

Examples 2 and 3 are directed to methods of converting a protected silylated clarithromycin oxime, particularly the preferred S-MOP oxime, to clarithromycin.

EXAMPLE 2

S-MOP oxime (20 g) is mixed with aqueous ethanol (120 ml) where the water to ethanol ratio is about 1:1 and sodium metabisulfite (13.6 g). Formic acid (2.6 g) is added and the mixture is stirred at about 80° C. to the reflux temperature to give clarithromycin. Heating is continued and the suspension is stirred for 2 hours. The mixture is then cooled to about 20° C. and sodium hydroxide solution in a concentration of about 47% is added at about this temperature until the pH reaches about 10.5. The solid is filtered and dried to give 8.3 g of clarithromycin, (about 78% based on assay).

EXAMPLE 3

S-MOP-oxime (20 g) was mixed with aqueous ethanol (120 ml) where the water to ethanol ratio is about 1:1 and sodium metabisulfite (13.6 g). Formic acid (2.6 g) was added and the mixture was stirred at reflux temperature for 3–4 hours. The second portion of sodium metabisulfite (13.6 g) was added and the reflux was continued for an additional 3–4 hours. The work up procedure was performed as described in Example 2. The crude clarithromycin was obtained (8.7 g, 82% based on assay) which after crystallization from ethanol gives essentially pure clarithromycin, which does not contain any detectable amount of clarithromycin oxime.

The present invention provides methods for preparing a protected silylated clarithromycin oxime and for converting a protected silylated clarithromycin oxime to clarithromycin. The invention further provides essentially oxime-free clarithromycin and compositions containing essentially oxime-free clarithromycin. Although the present invention has been described with respect to certain exemplary embodiments, such as those in which the method of preparing a protected silylated clarithromycin oxime includes reaction in the presence of specific solvents, bases, or methylating agents, there are many other variations of the above-described embodiments which will be apparent to those skilled in the art, even where elements or steps have not explicitly been designated as exemplary. It is understood that these modifications are within the teaching of the present invention.

We claim:

1. Clarithromycin comprising less than 40 ppm of its corresponding oxime intermediate as prepared by a process comprising the steps of:
   a) heating a mixture of C-2' and C-4" silylated protected clarithromycin oxime, formic acid and a deoximating agent, in a solvent comprising ethanol and water;
   b) thereafter adding an additional amount of deoximating agent; and
   c) isolating the clarithromycin, which contains its corresponding oxime intermediate at less than 40 ppm.

2. Clarithromycin comprising its corresponding oxime intermediate at less than 40 ppm, wherein the clarithromycin is formed by a method that includes converting a clarithromycin oxime intermediate to clarithromycin.

3. Clarithromycin comprising its corresponding oxime intermediate at less than 40 ppm, wherein the clarithromycin is formed by a method that includes converting 6-O-methyl-2', 4"-bis(trimethylsilyl)-erythromycin A 9-O-(2-methoxy prop-2-yl) oxime intermediate to the clarithromycin.

4. Clarithromycin comprising its corresponding oxime intermediate at less than 40 ppm, wherein the clarithromycin is prepared by a process comprising the steps of:
   a) heating a mixture of C-2' and C-4" silylated, protected clarithromycin oxime, formic acid and a deoximating agent, a solvent comprising ethanol and water at an ethanol to water ratio of about 1:1;
   b) thereafter adding an additional amount of deoximating agent; and
   c) isolating the clarithromycin.

5. Clarithromycin comprising S-MOP-oxime intermediate at less than 40 ppm, wherein the clarithromycin is formed by a method that includes converting a clarithromycin oxime intermediate to clarithromycin.

6. Clarithromycin comprising its corresponding oxime intermediate at less than 40 ppm, wherein the clarithromycin is formed by heating a mixture of 6-O-methyl-2', 4"-bis(trimethylsilyl)-erythromycin A 9-O-(2-methoxyprop-2-yl) oxime, formic acid and deoximating agent in an ethanol/water solvent at an ethanol to water ratio of about 1:1 to reflux for more than 4 hours, with a two-fold addition of said deoximating agent.

7. A pharmaceutical composition comprising the product of claim 1, 2, 3, 4, 5 or 6; and a pharmaceutically acceptable carrier.

8. The clarithromycin of claim 1, wherein the mixture in step b) is continued to reflux after the additional deoximating agent is added and until the deoximating is essentially complete.

9. Clarithromycin comprising its corresponding oxime intermediate at less than 40 ppm.

* * * * *